United States Patent [19]

Baxter et al.

[11] Patent Number: 5,698,706
[45] Date of Patent: Dec. 16, 1997

[54] HETEROCYCLIC AMIDES AND METHODS OF USE

[75] Inventors: Andrew Douglas Baxter; John Montana; David Alan Owen, all of Cambridge, United Kingdom

[73] Assignee: Chiroscience Limited, Cambridge, United Kingdom

[21] Appl. No.: 644,802

[22] Filed: May 10, 1996

[30] Foreign Application Priority Data

| May 10, 1995 | [GB] | United Kingdom | 9509432 |
| Dec. 15, 1995 | [GB] | United Kingdom | 9525644 |
| Apr. 4, 1996 | [GB] | United Kingdom | 9607256 |

[51] Int. Cl.⁶ .................. C07D 403/02; A61K 31/415
[52] U.S. Cl. .................. 548/314.7; 514/397

[58] Field of Search .................. 548/314.7; 514/396, 514/397

[56] References Cited

FOREIGN PATENT DOCUMENTS

| 0273689 | 7/1988 | European Pat. Off. | 514/396 |
| 2268933 | 1/1994 | United Kingdom | 514/396 |
| 8806890 | 9/1988 | WIPO | 514/396 |

*Primary Examiner*—Floyd D. Higel
*Attorney, Agent, or Firm*—Saliwanchik, Lloyd & Saliwanchik

[57] ABSTRACT

Peptidyl derivatives having a SH or acylS group and which are amides, primary amides or thioamides, have therapeutic utility via MMP or TNF inhibition.

24 Claims, No Drawings

HETEROCYCLIC AMIDES AND METHODS OF USE

FIELD OF THE INVENTION

This invention relates to a novel class of heterocyclic amide derivatives and their use in medicine.

BACKGROUND TO THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least four groups of metalloproteinases. These are the collagenases (interstitial collagenase, MMP-1; PMN collagenase, MMP-8, collagenase-3, MMP-13), the gelatinases (gelatinase A, MMP;2, 72kDa-gelatinase, Type IV collagenase; gelatinase B, MMP-9, 92kDa-gelatinase, Type IV. collagenase) the stromelysins (proteoglycanase, MMP-3, stromelysin-1, transin; stromelysin-2, MMP-10; stromelysin 3, MMP-11) and the membrane type matrix metalloproteinases (MT-1, MMP-14; MT-2, MMP-15; MT-3, MMP-16 and MT-4; MMP-17). Normally these catabolic enzymes are tightly regulated at the level of their synthesis and secretion and also at the level of their extracellular activity, the latter through the action of specific inhibitors, such as TIMP (tissue inhibitors of metalloproteinase), which form inactive complexes with metalloproteinases, and more general proteinase inhibitors such as $a_2$-macroglobulins.

The accelerated, uncontrolled breakdown of connective tissues by metalloproteinase catalysed resorption of the extracellular matrix is a feature of many pathological conditions such as rheumatoid arthritis, osteoarthritis, septic arthritis, corneal, epidermal or gastric ulceration; tumour metastasis or invasion; periodontal disease, proteinuria, coronary thrombosis associated with atherosclerotic plaque rupture and bone disease. Inhibitors may also be useful in preventing the pathological squaelae following a traumatic injury that could lead to a permanent disability. These compounds may also have utility as a means for birth control by preventing ovulation or implantation. It can be expected that the pathogenesis of such diseases is likely to be modified in a beneficial manner by the administration of metalloproteinase inhibitors and numerous compounds have been suggested for this purpose [for a general review see R C Wahl, et al Ann. Rep, Med. Chem. 25: 175–184, Academic Press Inc., San Diego (1990)].

A number of small peptide like compounds which inhibit metalloproteinases have been described. Perhaps the most notable of these are those relating to angiotensin converting enzyme (ACE) where such agents act to block the conversion of the decapeptide angiotensin I to angiotensin II, a potent pressor substance. Compounds of this type are described in EP-A-0012401. Also, related mercaptoamide peptidyl derivatives have shown ACE inhibitor activity in vitro and in vivo (H N Weller et al (1984), Biochem Biophys. Res. Comm., 125 (1):82–89).

TNF is a cytokine which is produced initially as a cell-associated 28kD precursor. It is released as an active, 17kD form (D-M. Jue et al, (1990) Biochemistry, 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal heamatopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al (1988) J. Clin. Invest. 81:1925–1937; Miethke et al (1992), J. Exp. Med. 175:91–98), post ischaemic reperfusion injury, malaria (Grau et al (1989), Immunol. Rev. 112:49–70); mycobacterial infection (Barnes et al (1992) Infect. Imm. 60:1441–6); meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Current clinical anti-TNF strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres S. (1991) Immunol. 72:56–60, Schandene et al (1992), Immunol. 76:30–34, Alegre ML, et al (1991); Transplantation 52:674–679, Bianco et al (1991) Blood 78: 1205–1221). Thalidomide has also been shown to inhibit TNF production by leucocytes (Sampajo et al (1991), J. Exp. Med.173:699–703). In experimental settings, anti-TNF monoclonal antibodies, soluble TNF receptors and soluble TNF receptor/immunoadhesins have been shown to specifically inhibit the effects of TNF action (Bagby et al (1991) J. Infect. Dis. 163:83–88, Charpentier et al. (1991) Pressemed. 20:2009–2011, Silva et al (1990) J. Infect. Dis. 162:421–427; Franks et al (1991) Infect. Immun. 59:2609–2614, Tracey et al (1987) Nature 330:662–664; Fischer et al (1992) PNAS USA in press, Lesslauer et al (1991) Eur. J. Immunol. 21:2883–2886, Ashkenazi et al (1991) PNAS USA 88: 10535–10539).

It has recently been shown that the effects of TNF are mediated by two peptides, TNFα and TNFβ. Although these peptides have only 3055 homology with each other, they activate the same receptors and are encoded by immediately adjacent genes. As used herein, the term turnout necrosis factor or TNF therefore means tumour necrosis factor a and peptides having a high degrees of sequence homology with, or substantially similar physiological effects to, TNFα, for example TNFβ.

One of the objectives of the present invention is to provide compounds which substantially inhibit the release of TNF from cells, and therefore may be used in the treatment of Conditions mediated by TNF. Such uses include, but are not limited to, the treatment of inflammation, fever, cardiovascular effects; haemorrhage, coagulation and acute phase response, cachexia and anorexia, acute infections, shock states; graft versus host reactions and autoimmune disease.

Compounds which have the property of inhibiting the action of metalloproteinases involved in connective tissue breakdown such as collagenase, stromelysin and gelatinase have been shown to inhibit the release of TNF both in vitro and in vivo (A J H Gearing et al (1994), Nature, 370:555-557; G M McGeehan et al (1994), Nature, 370:558-561: M J Crimmen et al, WO 93/20047). All of these reported inhibitors contain a hydroxamic acid zinc binding group.

It is, therefore, a further objective of this invention to provide compounds which, in addition to inhibiting TNF release, also inhibit the action of MMPs, and hence may be used in the treatment of patients who suffer from conditions mediated by TNF and/or MMPs.

As appreciated by those of skill in the art the significant proportion of homology between human fibroblast collagenase, stromelysin and gelatinase leads to the possibility that a compound that inhibits one enzyme may to some degree inhibit all of them.

Compounds that inhibit collagenase, which possess structural portions akin to those of the instant invention include those encompassed by U.S. Pat. No. 4,511,504 issued Apr. 16, 1985; U.S. Pat. No. 4,568,666, issued Feb 4, 1986.

Compounds of related structure that are claimed to inhibit stromelysin (proteoglycanase) are encompassed by U.S. Pat. No. 4,771,037, issued Sep. 13, 1988.

The applicants believe that stromelysin and collagenase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case et al (1989), J. Clin. Invest., 84:173-40; R. J. Williams et at (1990), Arth. Rheum., 33:533-41.

The applicants also believe that inhibitors of stromelysin, collagenase and gelatinase will be useful to control tumour metastasis, optionally in combination with current chemotherapy and/or radiation. See L. M. Matrisian et al (1986), Proc. Natl. Acad. Sci., USA, 83:9413-7; S. M. Wilhelm et al (1987), Ibid. 84:6725-29; Z. Werb et al (1989), J. Cell Biol., 109:872-889; L. A. Liotta et al (1983), Lab. Invest., 49:636-649; R. Reich et al in Metatasis; Ciba Foundation Symposium, Wiley, Chicester, 1988, pp. 193-210.

Secreted proteinases such as stromelysin, collagenase and gelatinase play an important role in processes involved in the movement of cells during metastasic tumour invasion. Indeed, there is also evidence that the matrix metalloproteinases are overexpressed in certain metastatic tumour cell lines. In this context, the enzyme functions to penetrate underlying basement membranes and allow the tumour cell to escape from the site of primary turnout formation and enter the circulation. After adhering to blood vessel wails, the turnout cells use these same metalloproteinases to pierce underlying basement membranes and penetrate other tissues, thereby leading to turnout metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts derived from inflamed gingiva (V. J. Uitto et al (1981), 1. Periodontal Res., 16:417-424). Enzyme levels have been correlated to the severity of gum disease; C. M. Overall et al (1987), J. Periodontal Res., 22:81-88.

Proteolytic processes have also been observed in me ulceration of the cornea following alkali burns (S. I. Brown et al (1969), Arch. Opthalmol., 81:370-373). MerCapto-containing peptides do inhibit the collagenase isolated from alkali-burned rabbit cornea (F. R. Burns et at (1989.), Invest. Opthalmol, 30:1569-1575). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine (W. H. Baricos et al (1989), Biochem. J., 254:609-612). Proteinuria, a result of glomerular disease, is excess protein in the urine caused by increased permeability of the GBM to plasma proteins. The underlying causes of the increased GBM permeability are unknown, but proteinases including stromelysin may play an important role in glomerular diseases. Inhibition of this enzyme may alleviate the proteinura associated with kidney malfunction.

It is suggested that inhibition of matrix metalloproteinase activity may prevent the rupturing of atherosclerotic plaques leading to coronary thrombosis. The tearing or rupture of atherosclerotic plaques is the most common event irritating coronary thrombosis. Destabilisation and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localised to individual cells in atherosclerotic plaques removed from heart transplant patients at the time of surgery (A. M. Henney et al (1991), Proc. Nat'l. Acad. Sci. USA, 88:8154-8158). Inhibition of stromelysin by these compounds may aid in preventing or delaying the degradation of the connective tissue matrix that stabilises the atherosclerotic plaques, thereby preventing events leading to acute coronary thrombosis.

It has been recently shown in a model of congestive heart failure (CHF) in the pig, that during CHF the are marked changes in the morphological structure of the heart. Ventricular dilation and wall thinning caused by changes to the extracellular matrix results in fewer collagen connections between cardiomyocytes and less total collagen. In such an instance a weaker force of contraction leads to an inefficient ventricular operation. It is believed that specific inhibitors of matrix metalloproteinases will play a key role in stabilising the extracellular matrix and therefore be important in the treatment and/or prevention of CHF.

It has recently been shown (WO 96/0240) that inhibitors of the matrix metalloproteinases, such as collagenase and stromelysin also inhibit the formation of human soluble CD23. CD23 is a 45 kDa type II integral protein expressed on the surface of a variety of mature cells, including B and T lymphocytes, macrophages, NK cells, Langerhans cells, monocytes, eosinophils and platelets (Delespesse et al, Adv. Immunology, 49,1991, 149; Grangette et al, J., Immunol, 143, 1989, 3580). Several activities have been ascribed to soluble CD23 in man, all of which involve IgE regulation. Particular activities include:

i) antigen presentation
ii) IgE mediated eosinophil cytotoxicity
iii) B Cell homing to lymph nodes and the spleen
iv) downregulation of IgE synthesis Thus, overall the excessive production of soluble CD23 has been implicated in the overproduction of IgE, the hallmark of allergic diseases such as extrinsic asthma, rhinitis, allergic conjunctivitis, eczema, atopic dermatitis and anaphylaxis (Sutton et al, Nature, 366, 1993, 421). Elevated levels of soluble CD23 have also been observed in the serum of patients with chronic B lymphocytic leukaemia (Safarti et al, Blood, 71, 1988, 94), and in the synovial fluid of patients with rheumatoid arthritis (Chomarat et al, Arthritis and Rheumatism, 36, 1993, 234).

It is therefore, a further objective of the present invention to provide compounds which inhibit the formation of human soluble CD23 for the production of a medicament for the treatment or prophylaxis of disorders such as allergy and autoimmune disease in which the overproduction of soluble CD23 is implicated, such as those described above.

Recent reports suggest that new enzymes of the MMP family also mediate the shedding of adhesion molecules such as the selectins, such as L-selectin. These soluble adhesion molecules are implicated in a number of diseases including cancer, autoimmunity and in the inflammatory response. It has been proposed that once cleaved, the selectin bind to particular ligands and this accounts for their biological activity. Thus, drugs that interfere with or prevent binding of the ligands to the selectins will be useful medicaments for treating a variety of the diseases described above. Therefore, it is a yet further objective of the present invention to provide compounds which inhibit the shedding of certain adhesion molecules and thus provide the production of a medicament for the treatment or prophylaxis of disorders such as cancer, autoimmune diseases or inflammatory diseases (such as inflammatory bowel disease and multiple sclerosis).

It is also believed that specific inhibitors of stromelysin and collagenase should be useful as birth control agents. There is evidence that expression of metalloproteinases, including stromelysin and collagenase, is observed in unfertilised eggs and zygotes and at further cleavage stages and increased at the blastocyst stage of fetal development and with endoderm differentiation (C. A. Brenner et al (1989), Genes & Develop., 3:848–59). By analogy to tumour invasion, a blastocyst may express metalloproteinases in order to penetrate the extracellular matrix of the uterine wall during implantation. Inhibition of stromelysin and collagenase during these early development processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation (J. F. Woessner et al (1989), Steroids; 54:491–499). There may also be a role for stromelysin activity during ovulation (C. K. L. Too et al (1984), Endocrin., 115:1043–1050).

Collagenolytic and stromelysin activity have also been observed in dystrophic epidermolysis bullosa (A. Kronberger et al (1982), I. Invest. Dermatol., 79:208–211; D. Sawamura et al (1991), Biochem. Biophys. Res. Commun., 184:1003–8). Inhibition of metalloendoproteinases should limit the rapid destruction of connective components of the skin.

In addition to extracellular matrix comprising structural components, stromelysin can degrade other in vivo substrates including the inhibitors $a_1$-proteinase inhibitor and may therefore influence the activities of other proteinases such as elastase (P. G. Winyard et al (1991), FEBS Letts., 279, 1:91–94). Inhibition of the matrix metalloendoproteinases may potentiate the antiproteinase activity of these endogenous inhibitors.

From recent publications it is evident that several new enzymes of the MMP family have been identified; some of which may be important in disease. Collagenase 3, an enzyme found in breast carcinoma tissue may have utility in breast cancer (IMP Freije et al (1994), J. Biol. Chem., 269 (24): 16766–16773) and other disease states; such as arthritis, whilst MT-MMPs, other members of the MMP family have been shown to be a key enzymes in the activation of gelatinase A (H Sato et al (1994), Nature, 370:61–65). Gelatinase A is an important enzyme in the growth and metastasis of tumours (such as defined above).

The degradation of β-Amyloid Precursor Protein (APP) has been shown to generate amyloid plaques, a major constituent of the senile plaques, found in patients with Alzheimers Disease (AD). Two recent publications have identified metalloproteinase enzymes that cleave APP to the amyloid plaque (C R Abraham et al (1994), Biochemistry, 33:192–199; G Huber et al (1994), Biochem. Biophys. Res. Comm., 201 (1):45–53).

As appreciated by those of skill in the art, the significant proportion of homology between these new enzymes and other MMPs leads to the possibility that a compound that inhibits one enzyme may to some degree inhibit these new enzymes. Therefore, inhibitors encompassed in this invention may be useful in the diseases in which these new enzymes are implicated.

SUMMARY OF THE INVENTION

The invention encompasses novel heterocyclic amides of formula (I) which are useful inhibitors of matrix metalloproteinase and/or TNF mediated diseases including degenerative diseases (such as defined above) and certain cancers.

In a first aspect of the invention there is provided a compound of general formula (I)

Wherein:

X is taken from the groups, including C=O and C=S;

$R^1$ is a $C_{1-6}$ alkyl, $C_{2-6}$ alkenyl, $C_{1-6}$ alkyl-aryl, $C_{1-6}$ alkyl-heteroaryl, or $C_{1-6}$ alkyl-$AR^4$ group where A is O, $NR^4$ or $S(O)_m$ where m=0-2, and $R^4$ is H, $C_{1-4}$ alkyl, aryl, heteroaryl, $C_{1-4}$ alkyl-aryl or $C_{1-4}$ alkyl-heteroaryl. If $A=NR^4$ the $R^4$ groups may be the same or different.

Y is heteroaryl (optionally substituted with $R^5$) $C_{1-4}$ alkyl-heteroaryl (optionally substituted with $R^5$) $C_{1-4}$ alkyl (optionally substituted with $R^5$) or heteroaryl (optionally substituted with $C_{1-4}$ alkyl-$R^5$) where $R^5$ is a OH, $OC_{1-4}$ alkyl, $COR^{13}$, $CO_2R^4$, $SO_2R^{13}$, $CON(R^4)_2$(where $R^4$ is the same or different), $SO_2N(R^4)_2$ (where $R^4$ is the same or different), $N(R^4)_2$(where $R^4$ is the same or different), $C_{1-4}$ alkyl, aryl, heteroaryl, $C_{1-4}$ alkyl-aryl or $C_{1-4}$ alkyl-heteroaryl group;

$R^2$ is hydrogen or the group $R^6$ CO where $R^6$ is a group $C_{1-4}$ alkyl, $C_{1-4}$ alkylaryl, $C_{1-4}$ alkyl-heteroaryl, cyclo $(C_{3-6})$ alkyl, $C_{1-4}$ alkyl-cyclo $(C_{3-6})$ alkyl, $C_{2-6}$ alkenyl, aryl or heteroaryl;

$R^3$ is hydrogen or aryl (optionally substituted with $R^7$), heteroaryl (optionally substituted with $R^7$), $C_{1-4}$ alkyl (optionally substituted with $R^7$), $C_{1-4}$ alkyl-aryl (optionally substituted with $R^7$), $C_{1-4}$ alkyl-heteroaryl (optionally substituted with $R^7$), cyclo ($C_{3-6}$) alkyl (optionally substituted with $R^7$), cyclo ($C_{3-6}$) alkenyl (optionally substituted with $R^7$), $C_{1-4}$ alkyl-cyclo ($C_{3-6}$) alkyl (optionally substituted with $R^7$) group, the groups

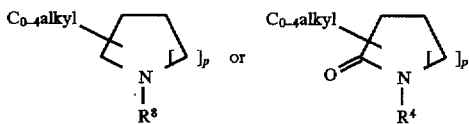

where p=1–2, or the group

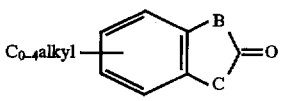

where B and C may be selected from the groups O, S, C($R^4$)$_2$, or $NR^4$ and these may be the same or different;

$R^7$ is $SR^2$, $CO_2R^{16}$, $SO_2R^{13}$, $SO_2N(R^4)_2$ (where $R^4$ may be the same or different), $N(R^4)_2$ (where $R^4$ may be the same or different), $NR^4R^8$, $NR^4R^{10}$, $OR^4$, $COR^{13}$, $COR^{14}$, $CON(R^4)_2$ (where $R^4$ may be the same or different), phthalimido or the groups

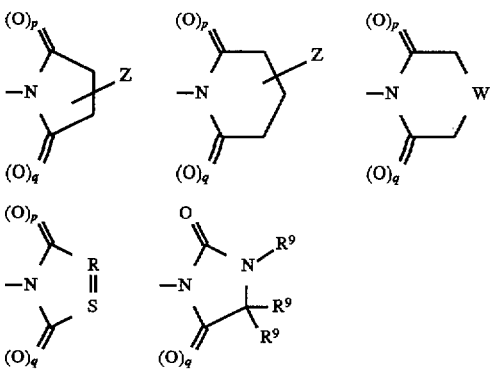

p and q may be 0 or 1 and may be the same or different;

R and S may be CH or N and may be the same or different;

W may be O, S(O)n where n=0–2 or $NR^{11}$;

Z may be H or $C_{0-4}$ alkyl-$R^{12}$ and may be attached to any available position on the ring;

$R^8$ is hydrogen or a $COR^{13}$, $CO_2R^{15}$, $CONHR^4$ or $SO_2R^{13}$ group;

$R^9$ is H or $C_{1-4}$ alkyl;

$R^{10}$ is $SO_2R^{14}$, or $COR^{14}$;

$R^{11}$ is H, $C_{1-4}$ alkyl, $COR^{13}$, $CO_2R^{15}$, $CON(R^4)_2$ (where $R^4$ maybe the same or different or $SO_2R^{13}$;

$R^{14}$ is $C_{1-4}$ alkyl (optionally substituted with $R^{12}$);

$R^{13}$ is $C_{1-4}$ alkyl, aryl, heteroaryl, $C_{1-4}$ alkyl-aryl or $C_{1-4}$ alkyl-heteroaryl;

$R^{15}$ is $C_{1-4}$ alkyl, $C_{1-4}$ alkyl-aryl or $C_{1-4}$ alkyl-heteroaryl;

$R^{16}$ is H, $C_{1-4}$ alkyl, $C_{1-4}$ alkyl-aryl or $C_{1-4}$ alkyl-heteroaryl;

$R^{12}$ may be $CO_2R^4$, $CON(R^4)_2$ (where $R^4$ maybe the same or different), $N(R^4)_2$ (where $R^4$ maybe the same or different), $SO_2R^{13}$ or the groups:

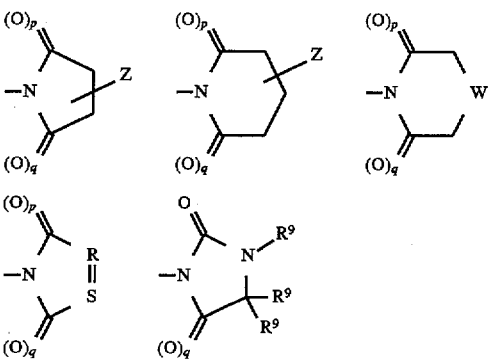

and the salts, solvates and hydrates thereof.

Preferred compounds of the invention include those in which, independently or in any combination have:

$R^1$ is $C_{1-6}$ alkyl or $C_{1-4}$ alkyl-$AR^4$ where A is $S(O)_m$, $NR^4$, or O and m=0, 1 or 2, and $R^4$ is H, $C_{1-4}$ alkyl, heteroaryl aryl;

$R^2$ is H or $COR^6$, where $R^6$ is alkyl or aryl;

X is C=O and Y is heteroaryl (optionally substituted with $R^5$ or $C_{1-4}$ alkyl-$R^5$), where $R^5$ maybe OH, O($C_{1-4}$ alkyl), $COR^{13}$, $CO_2R^4$ $CO(NR^4)_2$ (where $R^4$ is the same or different);

$R^3$ is $C_{1-4}$ alkyl-aryl (optionally substituted with $R^7$), $C_{1-4}$ alkyl-heteroaryl (optionally substituted with $R^7$), $C_{1-4}$ alkyl (optionally substituted with $R^7$), $C_{1-4}$ alkenyl (optionally substituted with $R^7$), cyclo($C_{3-6}$) alkyl (optionally substituted with $R^7$);

$R^7$ is $AR^4$, $CO_2R^{16}$, $NR^4R^8$, $CON(R^4)_2$ (where $R^4$ may be the same or different), phthalimido or succinimido;

$R^8$ is a $COR^{13}$, $CO_2R^{15}$, $CON(R^4)_2$ (where $R^4$ may be the same or different) or $SO_2R^{13}$ group;

$R^{13}$ is $C_{1-4}$ alkyl, aryl, heteroaryl, $C_{1-4}$ alkyl-aryl or $C_{1-4}$ alkyl-heteroaryl;

$R^{15}$ is $C_{1-4}$ alkyl, $C_{1-4}$ alkyl-aryl or $C_{1-4}$ alkyl-heteroaryl;

$R^{16}$ is H, $C_{1-4}$ alkyl, $C_{1-4}$ alkyl-aryl or $C_{1-4}$ alkyl-heteroaryl;

Compounds of the invention have $IC_{50}$ values below 50 µM against the MMP enzymes and/or below 50 µM in the whole cell assay of TNF inhibition.

It will be appreciated that the compounds according to the invention can contain one or more asymmetrically substituted carbon atoms, for example those marked with an asterisk in formula (I). The presence of one or more of these asymmetric centres in a compound of formula CI) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric centre to represent the possibility of R- and S- configurations, the < line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, tert-butyl, pentyl, hexyl and the like.

The term "$C_{1-4}$ alkyl" refers to a straight or branched chain alkyl moiety having from one to four carbon atoms, including for example, methyl, ethyl, propyl, isopropyl, butyl, tert-butyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cyclo ($C_{3-6}$) alkyl" refers to a saturated alicyclic moiety having from three to six carbon atoms and includes for example cyclopropyl, cyclobutyl, cyclopentyl, cyclohexyl and the like.

The term "cyclo ($C_{4-6}$) alkenyl" refers to an alicyclic moiety having from three to six carbon atoms and having in addition one double bond. This term would include for example cyclopentenenyl or cyclohexenyl.

There term "aryl" means an optionally substituted phenyl or naphthyl group with the substituent(s) being selected, for example, from halogen, trifluoromethyl, $C_{1-6}$ alkyl, alkoxy, phenyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a read fly clearable ester such as the methyl, ethyl, benzyl or tert-butyl ester.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "$C_{0-4}$ alkyl" refers to a straight or branched chain alkyl moiety having from zero to four carbon atoms, including for example, methyl, ethyl, propyl, isopropyl and the like.

The term "heteroaryl" refers to aromatic ring system of five to ten atoms or which at least one atom is selected from the group, O, N, or S and includes for example furanyl, thiophenyl, pyridyl, indolyl, quinolyl and the like.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2K^{17}$ where $R^{17}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trmethylbenzyloxymethyl or pivaloyloxymethyl group.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a particular stereoisomer of formula (I) is required, the synthetic processes described herein may be used with the appropriate homochiral starting material and/or isomers maybe resolved from mixtures using conventional separation techniques (eg. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, A, B, C, R, S, W, X, Y and Z are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts.

Thus the process required for preparing compounds of general formula (I) comprises of: deprotecting (for example by hydrolysis) a compound of general formula (II)

(II)

Wherein $R^2$ represents a suitable protecting group (eg tert-butyl, trityl, benzoate or acetate).

It will be appreciated that where a particular stereoisomer of formula (1) is required, this may be obtained by conventional resolution techniques such as high performance liquid chromatography. Where desired, however, appropriate homochiral starting materials may be used in the coupling reaction to yield a particular stereoisomer of formula (I). This is exemplified below: Where X is C=O, compounds of general formula (II) may be prepared by coupling an acid of formula (III).

(III)

Wherein $R^2$ and $R^3$ are as defined above, or an active derivative thereof, with an amine of formula (IV)

(IV)

where $R^1$ is defined previously, followed by removal of any protecting groups.

Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, eg. a cyclic ether such as tetrahydrofuran, an amide eg. a substituted amide such as dimethylformamide, or a halogenated hydrocarbon such as dichloromethane at a low temperature eg. −30° C. to ambient temperature, such as −20° C. to 0° C., optionally in the presence of as base, eg. an organic base such as an amine, eg. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

The acid of formula (III) may be prepared by nucleophilic substitution of compounds of formula (V)

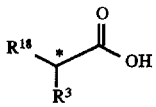
(V)

wherein $R^{18}$ represents a suitable leaving group (such as a halide eg bromide or a sulphonate ester eg methanesulphonate) as previously defined, with a thiol of general formula (VI).

(VI)

Acids of general formula (V) may be prepared either by halogenation of an acid of formula (VII) or by the Sandmeyer Reaction (diazotisation and concomitant halogenation) of an amino acid of formula (VIII).

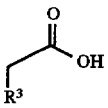
(VII)

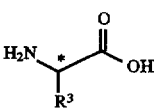
(VIII)

Acids of general formula (VII), may be readily obtained from commercially available starting materials using methods known to those skilled in the art. Many acids of general formula (VII) are also commercially available.

Amines of formula (IV) may be prepared from ketones of general formula (IX) by reductive amination or reduction of the corresponding oxime (X) which may be readily prepared from (IX).

T = O (IX)
T = NOH (X)

Ketones of general formula (IX) may be prepared by organometallic addition to a carboxylic acid of general formula (XI), or activated derivative thereof

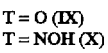
(XI)

Active derivatives of acids of formula (XI) include for example acid anhydrides, amides or acid halides, such as acid chlorides.

Acids of general formula (XI) may be readily obtained from commercially available starting materials using methods known to those skilled in the art. Many acids of general formula (XI) are also commercially available.

As a further extension to the invention, heterocycles such as imidazoles, oxazoles, thiazoles and triazoles may be prepared by cyclisation of a suitably protected aldehyde of general formula (XII)

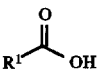
(XII)

followed by removal of any protecting groups.

Aldehydes of general formula (XII) may be prepared by reduction of suitably protected α-aminoacids of general formula (XIII)

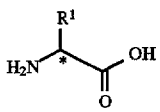
(XIII)

Amino acids and their derivatives as depicted by general formulae (VIII) and (XIII) can be obtained in optically pure or racemic form. In the homochiral form they provide asymmetric building blocks for the enantiospecific synthesis of compounds of general formula (I). Many of these derivatives can be readily obtained from commercially available starting materials using methods known to those skilled in the art. (See "The Practice of Peptide Synthesis" by M. Bodanszk et al, Springer Verlag, New York, 1984, P. L. Durette, WO92/21360).

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—eg ethanol) of a compound of formula (I) wherein $R^1$ is a $C_{2-6}$ alkenyl group. A further example would include a compound of formula (I) wherein $R^2$ is a group $R^6$ CO may be prepared by acylation (using a suitable acid chloride $R^6$ COCl, in the presence of a base such as a triethylamine in a suitable solvent, such as a chlorinated solvent—eg dichloromethane) of a compound of formula (I) wherein $R^2$ is H. Compounds where X is C=S may also be prepared by thioamidation, using Lawesson's Reagent for instance, of a compound where X is C=O.

Any mixtures of final products or intermediates obtained can be separated on the basis of the pysico-chemical differences of the constituents, in a known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example as described in Example A hereinafter.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

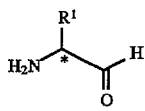
(XII)

As mentioned above, compounds of formula (I) are useful in human or veterinary medicine since they are active as inhibitors of TNF and MMPs. Accordingly in another aspect, this invention concerns:

- a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and
- a compound of formula (I) for use in human or veterinary medicine, particularly in the management (by which is meant treatment or prophylaxis) of diseases or conditions mediated by TNF and/or MMPs; and
- the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resportion,haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema and anaphylaxis.

For the treatment of rheumatoid arthritis, osteoarthritis, and in diseases and indications resulting from the overexpression of matrix metalloendoproteinases such as found in certain metastatic turnout cell lines or other diseases mediated by the matrix metalloendoproteinases or increased TNF production, the compunds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats; horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules, wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy- propylmethylcellulose, sodium alginate polyvinylpyrollidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents; such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occuring gums, for example gum acacia or gum tragacanth, naturally-occuring phosphatides, for example soya bean, lecithin, and esters or partial esters derived from fatty acids and hexitol anhydrides, for example sorbitan monooleate and condensation products of the said partial esters With ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above- indicated conditions (about 2.5 mg to about 7 gms per patient per day). for example, intimation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion. drug combination and the severity of the particular disease undergoing therapy.

The following non-limiting Examples are intended to illustrate the preparation of compounds of Formula (I), and as such are not intended to limit the invention as set forth in the claims.

In the Examples, the following abbreviations are used:

| | |
|---|---|
| RT | Room temperature |
| EDC | 1-(3-Dimethylaminopropyl)-3-ethyl carbodiimide hydrochloride |
| TNFα | Tumour necrosis factor α |
| LPS | Lipopolysaccharide |
| ELISA | Enzyme linked immunosorbent assay |

Intermediate 1 (R,S)-2-Acetylsuphanyl-5-phthalimidopentanoic acid
Prepared according to the procedure in WO-A-9611209.

Intermediate 2 (S)-N-(Benzyloxycarbonyl)leucinal

A solution of (S)-N-(benzyloxycarbonyl)teucioe methyl ester (8.22 g, 29.4 mmol) in dry toluene (80 ml) was treated dropwise at −78° C. with a solution of di-iso-butylaluminium hydride (1.0M, 74 ml, 74 mmol) in toluene. The solution was stirred at −78° C. for 30 min. before methanol (3.5 ml) was added to quench the reaction. The cold mixture was then added to a stirred aqueous solution of potassium hydrogen tartrate (200 ml). After further slitting for 1 hour the mixture was extracted with ether (3×200 ml), the combined extracts washed with brine (400 ml), dried (MgSO$_4$) and evaporated in vacuo to provide the title compound as a colourless oil. This material was used without purification in the next step.

Similarly prepared was:
Intermediate 3 (S)-N-(Benzyloxycarbonyl)phenylalaninal

From (S)-N-(benzyloxycarbonyl)phenylalanine methyl ester (8.0 g), as a colourless oil, which was used without purification in the next step.

Intermediate 4 2-[1-(N-Benzyloxycarbonylamino)-3-methylbutyl]imidazole

A solution of intermediate 2 (29.4 mmol) and glyoxal trimer dihydrate (10.36 g, 49.3 mmol) in methanol (150 ml) was treated at −15° C. with ammonia gas. After stirring for 4 hours at −10° C. the mixture was allowed to warm to RT and stirred overnight. The orange suspension was poured into water (400 ml) and the resulting white solid removed by filtration to provide the title compound 3.96 g, 47 %) as a white solid.

TLC R$_f$ 0.42 (5% MeOH—CH$_2$Cl$_2$)

Similarly prepared was:
Intermediate 5 2-[1-(N-Benzyloxycarbonylamino)-2-phenylethyl]imidazole From intermediate 3, as an off-white solid (4.1 g, 32%).
TLC R$_f$ 0.38 (5% MeOH—CH$_2$Cl$_2$)

Intermediate 6 (S)-2-[1-(N-Benzyloxycarbonylamino)-3-methylbutyl]-1-(1,1-dimethylethoxycarbonyl)imidazole A solution of di-tert-butyldicarbonate (5.47 g, 25 mmol) in dimethylformamide (80 ml) was added dropwise to a stirred solution of intermediate 4 (7.2 g, 25 mmol), di-iso-propylethylamine (4.35 ml, 25 mmol) and dimethylaminopyridine (92 me, 0.75 mmol) in dimethylformamide (140 ml) at 3° C. The mixture was allowed to warm slowly to RT and stirred overnight. The brown mixture was poured into water and extracted three times with ethyl acetate. The combined organic phases were washed three times with water and once with brine, dried (MgSO$_4$) and evaporated in vacuo to give the crude product as a brown oil. Purification by flash column chromatography on silica, eluting with 20% ethyl acetate-hexane, provided the desired product as a pale yellow oil. The oil was dissolved in dichloromethane (12 ml) and pentane (50 ml) was added. The mixture was placed in the freezer for 2 h alter which time the precipitate was removed by filtration and the filtrate was evaporated in vacuo to give the title compound (7.70 g, 20 mmol, 79%) as a pale yellow oil.

TLC R$_f$ 0.20 (33% ethyl acetate-hexane); ee assay 97.8%
Similarly prepared was:
Intermediate 7 (S)-2-[1-(N-Benzyloxycarbonylamino)-2-phenylethyl]-1-(1,1-dimethylethoxy carbonyl)imidazole From intermediate 5, as a pale yellow oil (3.52 g, 53%).
TLC R$_f$ 0.16 (33% ethyl acetate-hexane); ee assay 97.5%

Intermediate 8 (S)-2-[1-(N-Benzyloxycarbonylamino)-3-methylbutyl]imidazole

Trifluoroacetic acid (15.3 ml, 198 mmol) was added to a stiffed solution of intermediate 6 (7.5 g, 19.3 mmol) in dichloromethane at 3° C. The mixture was allowed to warm slowly to RT and stirred overnight. The mixture was evaporated in vacuo and then concentrated twice from a mixture of heptane and dichloromethane to give the title compound (5.53 g, 100%) as a white foam.

TLC $R_f$ 0.26 (5% methanol-dichloromethane)

Similarly prepared was:

Intermediate 9 (S)-2-[1-(N-Benzyloxycarbonylamino)-2-phenylethyl]imidazole

From intermediate 7, as a pale yellow foam (2.5 g, 100%)

TLC $R_f$ 0.32 (5% methanol-dichloromethane)

Intermediate 10 (S)-2-(1-Amino-3-methylbutyl)imidazole

A solution of intermediate 8 was hydrogenated at RT and atmospheric pressure over 10% palladium on carbon (50% w/w) in ethanol overnight. The catalyst was removed by filtration through hyflo and the filtrate evaporated to provide the crude title compound as a colourless foam, which was used directly in the next step.

Similarly prepared was:

Intermediate 11 (S)-2-(1-Amino-2-phenylethyl)imidazole

From intermediate 9, as a pale yellow foam, which was used directly in the next step without purification.

Example 1 2[(1S)-[(R,S)-2-Acetylsulphanyl-5-phthalimidopentanoylamino]-3-methylbutyl]-imidazole A solution of intermediate 1 (1 mmol) and intermediate 10 (1 mmol) in dry tetrahydrofuran (30 ml) was treated with N-hydroxybenzotriazole (1 mmol) and EDC (1 mmol) and the mixture stirred at RT overnight. The mixture was diluted with ethyl acetate (100 ml) and the solution washed with 8% sodium bicarbonate (50 ml), 1N hydrochloric acid (50 ml), water (50 ml) and brine (50 ml), dried (MgSO$_4$) and evaporated in vacuo to a pale yellow foam. Purification by flash column chromatography on silica, eluting with 2–3% methanol-dichloromethane, provided the title compound (43%) as a colourless foam.

TLC $R_f$ 0.32 (5% MeOH—CH$_2$Cl$_2$)

Similarly prepared was:

Example 2 2-[(1S)-[(R,S)-2-Acetylsulphanyl-5-phthalimidopentanoylamino]-2-phenylethyl]-imidazole From intermediate 1 and intermediate 11, as a white solid (270 mg, 49%).

TLC $R_f$ 0.36 (5% MeOH—CH$_2$Cl$_2$)

Example 3 2-[(1S)-[(R,S)-2-Acetylsulphanyl-5-phthalimidopentanoylamino]-2-phenylethyl]-imidazole Aqueous ammonia solution (0.88 SG, 0.8 ml) was added to a stirred solution of example 2 (200 mg, 0.33 mmol) in 25% dichloromethane-methanol at 3° C. under a nitrogen atmosphere. The mixture was stirred for 90 min before being warmed to RT and stirred for a further 1 h. The mixture was concentrated in vacuo to give a white solid. Purification by flash column chromatography on silica, during with 2 % methanol-dichloromethane, provided the title compound (148 mg, 79%) as a white solid.

TLC $R_f$ 0.26 (5% methanol-dichloromethane)

Similarly prepared was;

Example 4 2-[(1S)-[(R,S)-2-Acetylsulphanyl-5-phthalimidopentanoylamino]-3-methylbutyl]-imidazole From example 1, as a white solid (200 mg, 82%).

TLC $R_f$ 0.32 (5% methanol-dichloromethane)

Example A

Collagenase inhibition activity

The potency of compounds of general formula (I) to act as inhibitors of collagenase was determined by the procedure of Cawston and Barrett (Anal. Biochem., 99:340–345, 1979) whereby a 1 mM solution of the inhibitor being tested or dilutions thereof was incubated at 37° C. for 16 hours with collagen and collagenase (buffered with 50 mM Tris, pH 7.6 containing 5 mM CaCl$_2$, 0.05% Brij 35, 60 mM NaCl and 0.02% NaN$_3$). The collagen was acetylated $^3$H or $^{14}$C-collagen prepared by the method of Cawston and Murphy (Methods in Enzymology, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the molts reported as that inhibitor concentration effecting 50% inhibition of the collagenase (IC$_{50}$).

Example B

Stromelysin inhibition activity

The potency of compounds of general formula (I) to act as inhibitors of stromelysin was determined using the procedure of Nagase et al (Methods in Enzymology Vol 254, 1994), whereby a 0.1 mM solution of the inhibitor being tested or dilutions thereof was incubated at 37° C. for 16 hours with stromelysin and $^3$H transferrin (buffered with 50 mM Tris, pH 7.6 containing 10 mM CaCl$_2$, 150 M NaCl, 0.05% Brij, 35, and 0.02% NaN$_3$). The transferrin was carboxymethylated with $^3$H iodoacetic acid. The stromelysin activity in the presence of 1 mM, or a dilution thereof, was compared to a control devoid of inhibitor and the results reported as that inhibitor concentration effecting 50% inhibition of the stromelysin (IC$_{50}$).

Example C

Gelatinase inhibition activity

The potency of the compounds of general formula (I) to act as inhibitors of gelatinase was determined using the procedure of Harris & Krane (Biochem Biophys. Acta, 258:566–576, 1972), whereby a 1 mM solution of the inhibitor being tested or dilutions thereof was incubated at 37° C. for 16 hours with gelatinase and heat denatured $^3$H or $^{14}$C-acetylated collagen (buffered with 50 mM Tris, pH 7.6 containing 5 mM CaCl$_2$, 0.05% Brij 35 and 0.02% NAN$_3$). The $^3$H or $^{14}$C gelatin was prepared by denaturing $^3$H or $^{14}$C-collagen produced according to the method of Cawston and Murphy (Methods in Enzymology, 80:711, 1981) by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase (IC$_{50}$).

Example D

MMP Inhibition Activity-Fluorimetric Assay

The potency of compounds of general formula (I) to act as inhibitors of collagenase-1(MMP-1), collagenase-2 (MMP-8), gelatinase-A (MMP-2), gelatinase-B (MMP-9) and stromelysin-1(MMP-3) was determined using the following procedure: Inhibitors were dissolved in dimethylsulphoxide containing 0.02% b-mercaptoethanol and serial dilutions are prepared. Activated enzyme was incubated in assay buffer containing 50 mM Tris, pH 7.4, 5mM CaCl$_2$, 0.002% NaN$_3$ and Brij 35 in the presence and absence of inhibitor. Samples were preincubated at 37° C. for 15 minutes before the addition of the fluorimetric substrate (Mca-Pro-Leu-Dpa-Ala-Arg-NH$_2$) to a final concentration of 10 mM. The assay was incubated for 90 minutes at 37° C. and then read in a Fluoroscan II at $1_{ax}$ (355 nm) and $1_{cm}$ (460 nm). The enzyme activity was compared to activity in a control devoid of inhibitor and the results reported as that inhibitor concentration effecting 50% inhibition of the stromelysin (IC$_{50}$).

Example E
Inhibition of TNFα production

The potency of the compounds of general formula (I) to act as inhibitors of the production of TNFa was determined using the following procedure: A 1 mM solution of the inhibitor being tested or dilutions thereof was incubated at 37° C. in an atmosphere of 5% $CO_2$ with THP-1 cells (human monocytes) suspended in RPM1 1640 medium and 20 μM β-mercaptoethanol at a cell density of $1\times10^6$/ml and stimulated with 5 μg/ml final concentration of LPS. After 18 hours the supernatant was assayed for the levels of TNFα using a commercially available ELISA kit (R & D Systems). The activity in the presence of 0.1 mM inhibitor or dilutions thereof was compared to activity in a control devoid of inhibitor and results reported as that inhibitor concentration offcoting 50% inhibition of the production of TNFa.

Example F
Adjuvant arthritic rat model

Compounds of general formula (I) were evaluated in an adjuvant arthritis model in the rat based on the methods employed by B. B. Newbould (1963), Br.J.Pharmacol, 21, 127–136 and C. M. Pearson and F. D. Wood. (1959), Arthritis Rheum, 2, 440–459. Briefly, male Wistar rats (180–200 g) were injected at the base of the tail with Freund's adjuvant. Twelve days later the responding animals were randomised into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over day 12 values.

Example G
Mouse ovarian carcinoma xenograft model

Compounds of general formula (I) were evaluated in an ovarian carcinoma xenograft model of cancer, based on that described by B. Davies et al (1993), Cancer Research, 53, 2087–2091 This model, in brief, consists of inoculating female nu/nu mice with $1\times10^9$ OVCAR3-icr cells into the peritoneal cavity. Compound of general formula (I) are administered by the oral route as a suspension in 1% methyl cellulose or intraperitoneally as a suspension in phosphate buffered saline in 0.01% Tween-20. At the conclusion of the experiment (4–5 weeks) the number of peritoneal cells are counted and any solid tumour deposits weight. In some experiments turnout development is monitored by measurement of tumour specific antigens.

Example H
Rat mammary carcinoma mode

Compounds of general formula (I) were evaluated in a HOSP.1 rat mammary carcinoma model of cancer (S. Eccles et al (1995), Cancer Research, in press). This model consists of the intravenous inoculation of female CBH/cbi rats with $2\times10^4$ tumour cells into the jugular vein. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the animals were killed, the lungs were removed and individual tumours counted after 20 hours fixation in Methacarn.

We claim:

1. A compound of the formula (I)

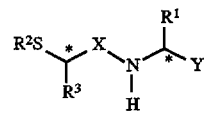

wherein:

X is selected from the group consisting of C=O and C=S;

$R^1$ is a $C_{1-6}$ alkyl, $C_{2-6}$ alkenyl, $C_{1-6}$ alkyl-aryl, $C_{1-6}$ alkyl-heteroaryl, or $C_{1-6}$ alkyl-$AR^4$ group where A is O, $NR^4$ or $S(O)_m$ where m=0–2, and $R^4$ is H, $C_{1-4}$ alkyl, aryl, heteroaryl, $C_{1-4}$ alkyl-aryl or $C_{1-4}$ alkyl-heteroaryl; if $A=NR^4$ the $R^4$ groups may be the same or different;

Y is heteroaryl (optionally substituted with $R^5$), $C_{1-4}$ alkyl-heteroaryl (optionally substituted with $R^5$), $C_{1-4}$ alkyl (optionally substituted with $R^5$) or heteroaryl (optionally substituted with $C_{1-4}$ alkyl-$R^5$) where $R^5$ is a OH, $OC_{1-4}$ alkyl, $COR^{13}$, $CO_2R^4$, $SO_2R^{15}$, CON $(R^4)_2$ (where $R^4$ is the same or different), $SO_2N(R^4)_2$ (where $R^4$ is the same or different), $N(R^4)_2$ (where $R^4$ is the same or different), $C_{1-4}$ alkyl, aryl, heteroaryl, $C_{1-4}$ alkyl-aryl or $C_{1-4}$ alkyl-heteroaryl group;

$R^2$ is hydrogen or the group $R^6$ CO where $R^6$ is a group $C_{1-4}$ alkyl, $C_{1-4}$ alkylaryl, $C_{1-4}$ alkyl-heteroaryl, cyclo $(C_{3-6})$alkyl, $C_{1-4}$ alkyl-cyclo $(C_{3-6})$alkyl, $C_{2-6}$ alkenyl, aryl or heteroaryl;

$R^3$ is hydrogen or aryl (optionally substituted with $R^7$), heteroaryl (optionally substituted with $R^7$), $C_{1-4}$ alkyl (optionally substituted with $R^7$), $C_{1-4}$ alkyl-aryl (optionally substituted with $R^7$), $C_{1-4}$ alkyl-heteroaryl (optionally substituted with $R^7$), cyclo($C_{3-6}$)alkyl (optionally substituted with $R^7$), cyclo ($C_{3-6}$) alkenyl (optionally substituted with $R^7$), $C_{1-4}$ alkyl-cyclo($C_{3-6}$) alkyl (optionally substituted with $R^7$) group, the groups

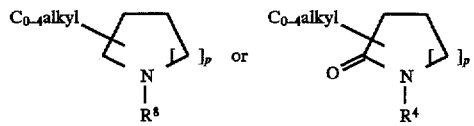

where p=1–2, or the group

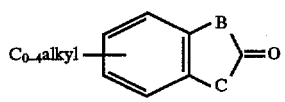

where B and C may be selected from the groups O,S,C $(R^4)_2$, or $NR^4$ and these are the same or different;

$R^7$ is $SR^2$, $CO_2R^{16}$, $SO_2R^{13}$, $SO_2N(R^4)_2$ (where $R^4$ may be the same or different), $N(R^4)$ (where $R^4$ may be the same or different), $NR^4R^8$, $NR^4R^{10}$, $OR^4$, $COR^{13}$, $COR^{14}$, $CON(R^4)_2$ (where $R^4$ may be the same or different), phthalimido or the groups

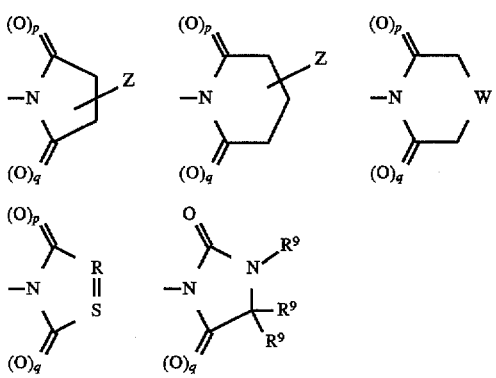

p and q may be 0 or 1 and may be the same or different;
R and S may be CH or N and may be the same or different;
W may be O, $S(O)_n$ where n=0–2 or $NR_n$;
Z may be H or $C_{0-4}$ alkyl-$R^{12}$ and may be attached to any available position on the ring;
$R^8$ is hydrogen or a $COR^{13}$, $CO_2R^{15}$, $CONHR^4$ or $SO_2R^{13}$ group;
$R^9$ is H or $C_{1-4}$ alkyl;
$R^{10}$ is $SO_2R^{14}$, or $COR^{14}$;
$R^{11}$ is H, $C_{1-4}$ alkyl, $COR^{13}$, $CO_2R^{15}$, $CON(R^4)_2$ (where $R^4$ maybe the same or different) or $SO_2R^{13}$;
$R^{14}$ is $C_{1-4}$ alkyl (optionally substituted with $R^{12}$);
$R^{13}$ is $C_{1-4}$ alkyl, aryl, heteroaryl, $C_{1-4}$ alkyl-aryl or $C_{1-4}$ alkyl-heteroaryl;
$R^{15}$ is $C_{1-4}$ alkyl, $C_{1-4}$ alkyl-aryl or $C_{1-4}$ alkyl-heteroaryl;
$R^{16}$ is H, $C_{1-4}$ alkyl, $C_{1-4}$ alkyl-aryl or $C_{1-4}$ alkyl-heteroaryl;
$R^{12}$ may be $CO_2R^4$, $CON(R^4)_2$ (where $R^4$ maybe the same or different), $N(R^4)_2$ (where $R^4$ maybe the same or different), $SO_2R^{13}$ or the groups:

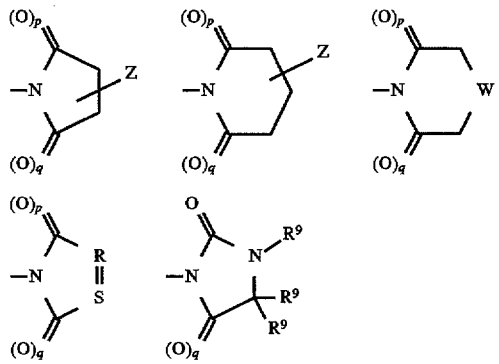

or the salts, solvates or hydrates thereof.

2. The compound of claim 1, wherein $R^1$ is $C_{1-6}$ alkyl or $C_{1-4}$ alkyl-$AR^4$ where A is $S(O)_m$, $NR^4$, or O and m=0, 1 or 2, and $R^4$ is H, $C_{1-4}$ alkyl, heteroaryl or aryl.

3. The compound of claim 1, wherein $R^2$ is H or $COR^6$, where $R^6$ is alkyl or aryl.

4. The compound of claim 1, wherein X is C=O and Y is heteroaryl (optionally substituted with $R^5$ or $C_{1-4}$ alkyl-$R^5$), where $R^5$ is OH, O($C_{1-4}$ alkyl), $COR^{13}$, $CO_2R^4$ or $CO(NR^4)_2$ (where $R^4$ is the same or different).

5. The compound of claim 1, wherein is $R^3$ is $C_{1-4}$ alkyl-aryl (optionally substituted with $R^7$), $C_{1-4}$ alkyl-heteroaryl (optionally substituted with $R^7$), $C_{1-4}$ alkyl (optionally substituted with $R^7$), $C_{1-4}$ alkenyl (optionally substituted with $R^7$) or cyclo($C_{3-6}$) alkyl (optionally substituted with $R^7$).

6. The compound of claim 1, wherein $R^7$ is $AR^4$, $CO_2R^{16}$, $NR^4R^8$, $CON(R^4)_2$ (where $R^4$ may be the same or different), phthalimido or succinimido.

7. The compound of claim 1, wherein $R^8$ is $COR^{13}$, $CO_2R^{15}$, $CON(R^4)_2$ (where $R^4$ may be the same or different) or $SO_2R^{13}$.

8. The compound of claim 1, wherein $R^{13}$ is $C_{1-4}$ alkyl, aryl, heteroaryl, $C_{1-4}$ alkyl-aryl or $C_{1-4}$ alkyl-heteroaryl.

9. The compound of claim 1, wherein $R^{15}$ is $C_{1-4}$ alkyl, $C_{1-4}$ alkyl-aryl or $C_{1-4}$ alkyl-heteroaryl.

10. The compound of claim 1, wherein $R^{16}$ is H, $C_{1-4}$ alkyl, $C_{1-4}$ alkyl-aryl or $C_{1-4}$ alkyl-heteroaryl.

11. The compound of claim 1, wherein Y is optionally-substituted heteroaryl, alkyl-heteroaryl or alkyl; and $R^7$ is $SR^2$, $COOR^{16}$ where $R^{16}$ is H or alkyl, $SO_2R^{13}$, $SO_2N(R^4)_2$, $N(R^4)_2$, $NR^4R^8$, $OR^4$, $COR^{13}$, phthalimido or succinimido.

12. The compound of claim 1, which is
2-[(1S)-[(R,S)-2-acetylsuphanyl-5-phthalimidopentanoylamino]-3-methylbutyl] imidazole.

13. The compound of claim 1, selected from the group consisting of
2-[(1S)-[(R,S)-2-acetylsulphanyl-5-phthalimidopentanoylamino]-2-phenylethyl]imidazole
2-[(1S)-[(R,S)-2-sulphanyl-5-phthalimidopentanoylamino]-2-phenylethyl]imidazole and
2-[(1S)-[(R,S)-2-sulphanyl-5-phthalimidopentanoylamino]-3-methylbutyl] imidazole.

14. The compound of claim 1, in the form of a single enantiomer or diastereomer, or a mixture of such isomers.

15. A pharmaceutical composition for use in therapy, comprising a compound of claim 1, and a pharmaceutically-acceptable diluent or carrier.

16. A method for the treatment of a condition associated with matrix metalloproteinases or that is mediated by TNFα, comprising administering an effective amount of the compound of claim 1 to a person or animal in need of such treatment.

17. The method according to claim 16, wherein the condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia and anorexia, acute infection, HIV infection, shock states, graft versus host reactions, autoimmune disease, reperfusion injury, meningitis and migraine.

18. The method according to claim 16, wherein the condition is selected from the group consisting of tumour growth, angiogenesis, tumour invasion and spread, metastases, malignant ascites and malignant pleural effusion.

19. The method according to claim 16, wherein the condition is selected from the group consisting of rheumatoid arthritis, osteoarthritis, osteoporosis, asthma, multiple sclerosis, neurodegeneration, Alzheimer's, stroke, vasculitis, Crohn's disease and ulcerative colitis.

20. The method according to claim 16, wherein the condition is selected from the group consisting of corneal ulceration, retinopathy and surgical wound healing.

21. The method according to claim 16, wherein the condition is selected from the group consisting of psoriasis, atopic dermatitis, chronic ulcers and epidermolysis bullosa.

22. The method according to claim 16, wherein the condition is selected from the group consisting of periodontitis and gingivitis.

23. The method according to claim 16, wherein the condition is selected from the group consisting of rhinitis, allergic conjunctivitis, eczema and anaphylaxis.

24. The method according to claim 16, wherein the condition is selected from the group consisting of atherosclerosis and congestive heart failure.

* * * * *

UNITED STATES PATENT AND TRADEMARK OFFICE
CERTIFICATE OF CORRECTION

PATENT NO. : 5,698,706

DATED : December 16, 1997

INVENTOR(S) : Andrew Douglas Baxter, John Montanan, David Alan Owen

It is certified that error appears in the above-identified patent and that said Letters Patent is hereby corrected as shown below:

Column 20, line 26: "$SO_2R^{15}$" should read --$SO_2R^{13}$--; and line 64: "$N(R^4)$" should read --$N(R^4)_2$--.

Column 21, line 19: "$NR_n$" should read --$NR^{11}$--; and line 65: "wherein is $R^3$ is" should read --wherein $R^3$ is--.

Signed and Sealed this

Tenth Day of March, 1998

*Attest:*

BRUCE LEHMAN

*Attesting Officer*      Commissioner of Patents and Trademarks